United States Patent [19]

Marinangeli et al.

[11] Patent Number: 5,491,271
[45] Date of Patent: Feb. 13, 1996

[54] DETERGENT ALKYLATION USING A REGENERABLE CLAY CATALYST

[75] Inventors: Richard E. Marinangeli, Arlington Heights; Jennifer S. Holmgren, Bloomingdale, both of Ill.

[73] Assignee: UOP, Des Plaines, Ill.

[21] Appl. No.: 296,391

[22] Filed: Aug. 26, 1994

[51] Int. Cl.[6] .................................................. C07C 2/66
[52] U.S. Cl. .............................. 585/468; 502/20; 502/31; 585/446
[58] Field of Search ...................... 502/20, 31; 585/446, 585/467, 468

[56] References Cited

U.S. PATENT DOCUMENTS 5,034,564  7/1991  Kocal ....................................... 585/467
5,118,897  6/1992  Khonsari et al. .......................... 585/467
5,358,915  10/1994  Nebergall et al. ......................... 502/27

*Primary Examiner*—Ponnathapura Achutamurthy
*Attorney, Agent, or Firm*—Thomas K. McBride; Eugene I. Snyder

[57] ABSTRACT

Tetrahedrally charged clays have been found to be active, regenerable catalysts in detergent alkylation, both as delaminated and pillared clays. The pillared saponites and beidellites are especially favored in forming detergent range alkylates using olefins as the alkylating agent to afford products with high monoalkylation selectivity and high linearity. Catalysts can be regenerated by a benzene wash or, after severe deactivation, by a carbon burn.

14 Claims, No Drawings

DETERGENT ALKYLATION USING A REGENERABLE CLAY CATALYST

BACKGROUND OF THE INVENTION

Over fifty years ago it was recognized that alkylbenzene sulfonates (ABS) were quite effective detergents superior to natural soaps in many respects. Because of their lower price, their price stability, and their effectiveness in a wide range of detergent formulations, ABS rapidly displaced soaps in household laundry and dishwashing applications and became the standard surfactants for the detergent industry.

The alkylbenzene sulfonates as initially prepared had substantial branching in the alkyl chain. This situation was maintained until the early 1960's when it became apparent that the branched alkyl-based detergents were contributing to the pollution of lakes and streams and forming relatively stable foams. Examination of the problem showed that the branched structure of the alkyl chains was not susceptible to rapid biodegradation and the surfactant properties of the detergent thus persisted for long periods of time. This was not the case earlier when natural soaps were used, because of the rapid biodegradation of the linear chains in natural soaps.

After recognizing the biodegradability of ABS based on alkylation by linear olefins, industry turned its attention to the production of these unbranched olefins and their subsequent use in the production of linear alkyl benzenes. Processes were developed for efficient alkylation of benzene by available feedstocks containing linear olefins, and the production of linear alkyl benzenes (LAB) became another reliable process broadly available to the petroleum and petrochemical industry. It gradually evolved that HF-catalyzed alkylation was particularly effective in LAB production, and an HF-based alkylation process became the industry standard.

With increasing environmental concern came increasing disenchantment with HF as a catalyst and a concomitant need to find a substitute equal or superior to it in all respects. As regards criteria in addition to the price, the extent of conversion effected by the catalyst, the selectivity of monoalkylbenzene formation, and the linearity of alkylbenzenes produced loomed large. At this point the definition of several terms are necessary to adequately understand and appreciate what follows.

Alkylation typically is performed using an excess of benzene relative to olefins. The ideal catalyst would show 100% conversion of olefins using an equal molar proportion of benzene and olefins, but since this has not been attainable one strives for maximum olefin conversion using a benzene to olefin molar ratio up to about 30. The better the catalyst, the lower will be the benzene:olefin ratio at a high conversion of, say, 98%. The degree of conversion at a constant value of benzene-olefin ratio is a measure of catalytic activity (subject to the caveat that the ratio must not be so high that the degree of conversion is invariant to small changes in this ratio). The degree of conversion may be expressed by the formula, $$V=C/T \times 100,$$

where V equals percent conversion, C equals moles of olefin consumed, and T equals moles olefin initially present.

However active the catalyst may be, it is not valuable unless it also is selective. Selectivity is defined as the percentage of total olefin consumed under reaction conditions which appears as monoalkylbenzene and can be expressed by the equation, $$S=M/C \times 100,$$

where S equals selectivity, M equals moles of monoalkylbenzenes produced, and C equals moles olefin consumed. The better the selectivity, the more desirable is the catalyst. An approximate measure of selectivity is given by the equation, $$S = \frac{\text{weight monoalkylbenzene}}{\text{weight total products}} \times 100$$

where "total products" includes monoalkylbenzenes, polyalkylbenzenes, and olefin oligomers. At high selectivity (S>85%) the results calculated from the two equations are nearly identical. The latter of the foregoing two equations is routinely used in commercial practice because of the difficulty in distinguishing between oligomers and polyalkylbenzenes.

Finally, the reaction of linear olefins with benzene in principal proceeds according to the equation,

Note that the side chain is branched solely at the benzylic carbon and contains only one branch in the chain. Although strictly speaking this is not a linear alkylbenzene, nonetheless the terminology which has grown up around the process and product in fact includes as linear alkylbenzenes those materials whose alkyl group chemically arises directly from linear olefins and therefore includes alpha-branched olefins. Because alkylation catalysts also may induce the rearrangement of olefins to give products which are not readily biodegradable (vide supra), for example, α,α-disubstituted olefins which subsequently react with benzene to afford an alkyl benzene with branching at other than the benzylic carbon,

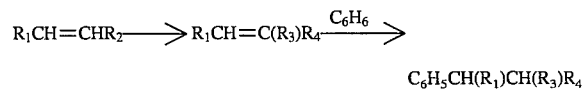

the degree to which the catalyst effects formation of linear alkyl benzenes is another important catalyst parameter. The degree of linearity can be expressed by the equation, $$D=L/M \times 100,$$

where D equals degree of linearity, L equals moles of linear monoalkyl benzene produced, and M equals moles of monoalkyl benzene produced.

Consequently, the ideal catalyst is one where V equals 100, S equals 100, and D equals 100. The minimum requirement is that linearity be at least 90% at a selectivity of at least 85% and an initial conversion of at least 98%. These are minimum requirements; that is, if a catalyst fails to meet all of the foregoing requirements simultaneously the catalyst is commercially unacceptable.

The linearity requirement is assuming added importance and significance in view of the expectation in some areas of minimum standards for linearity in detergents of 92–95% near-term, increasing to 95–98% by about the year 2000. Since the olefinic feedstock used for alkylation generally contains a small percentage of non-linear olefins—a non-liner olefin content of about 2% is common to many processes—the requisite linearity in the detergent alkylate places even more stringent requirements on catalytic performance; the inherent linearity of the alkylation process must increase by the amount of non-linear olefins present in the feedstock. For example, with a feedstock containing 2% non-linear olefins the catalyst must effect alkylation with 92% linearity in order to afford a product with 90% linearity, and with a feedstock containing 4% non-linear olefins the catalyst must effect alkylation with 94% linearity to achieve the same result.

Clays of diverse type are known catalysts for detergent alkylation. We have observed for some time that clays as a group afford detergent alkylates with significantly higher linearity under comparable reaction conditions than do other detergent alkylation catalysts such as silica-aluminas and zeolites. However, commercial development of clays as alkylation catalysts has been hampered by their resistance to regeneration. Thus, in detergent alkylation quite typically one employs reaction conditions which affords 99–100% conversion of olefin with fresh catalyst. Deactivation of catalyst occurs invariably leading to a decrease in olefin conversion, and when olefin conversion is reduced by some predetermined amount relative to its initial conversion the catalyst is removed from service and treated so as to restore its activity to that approximately equal to fresh catalyst. This process is referred to as catalyst regeneration, and the preferred mode of catalyst regeneration is a simple benzene wash at a temperature at least equal to, but usually in substantial excess of, the alkylation temperature. Catalyst reaction cycles frequently may be on the order of 24 hours with the regeneration cycles on the order of 24 hours. That is, the material is used as a catalyst for about 24 hours, and then its activity is restored with a benzene wash over a like period of time. Whereas the foregoing regeneration procedure works admirably with, for example, silica-alumina, which we use as our reference catalyst, we have consistently found over many years of experimental observation that clays fail to respond to the foregoing method of regeneration.

Additionally, it is a more-or-less standard observation that after some number of benzene wash cycles the lifetime of a catalyst is considerably shortened, i.e., even though catalyst activity is restored the time over which it becomes deactivated gradually decreases until the reaction cycle time of the catalyst is so short as to make catalyst use impractical. At this point the deactivated catalyst usually is subjected to the more severe regeneration procedure of a carbon burn, i.e., a high temperature treatment with oxygen to remove all organic materials and coke from the catalyst surface. Although materials such as silica-aluminas respond well to a carbon burn, with complete restoration of activity and catalyst lifetime, we have observed that clays generally do not so respond. Evidently the condition under which a carbon burn occurs destroys the clay structure, often deactivating the clay entirely.

Another generic disadvantage of clays relative to the silica-aluminas is that generally they are less active and less stable. That is, at the same alkylation conditions clays generally are substantially less active than other alkylation catalysts, and generally have shorter lifetimes (i.e., lower stability) before regeneration becomes necessary.

Particularly in view of our consistent observations of relative non-regenerability of clays, it came as quite a surprise to find that tetrahedrally charged clays, whether delaminated or pillared, form a class of clays which are readily regenerated by a benzene solvent wash. The class of tetrahedrally charged clays is represented by saponite and beidellite as its most important and well-known examples. We were further surprised to find that the tetrahedral clays, such as pillared saponite and beidellites, exacted no activity penalty relative to, for example, the silica-aluminas. In particular, pillared saponites and beidellites are substantially more active than other clays, especially when calcined at relatively low temperatures, showing an activity comparable to silica-aluminas and exhibiting a like linearity. Summarizing, the pillared saponites and beidellites show behavior more similar to silica-aluminas as a detergent alkylation catalyst than to other clays.

We mention in passing that clays of diverse type are known catalysts for detergent alkylation. In U.S. Pat. No. 5,034,564 the patentee noted the combination of a pillared clay and a binder, including pillared clays based on saponite and beidellite, was useful in detergent alkylation. However, even here there was no teaching, nor even a suggestion, of regenerability. In fact, there was no distinction made between the non-regenerable octahedrally-charged pillared montmorillonite and the regenerable, tetrahedrally-charged pillared saponite and beidellite of this invention. Consequently it can be fairly stated that the prior art was devoid of any hint or suggestion of our invention.

SUMMARY OF THE INVENTION

The purpose of this invention is to provide a method of alkylating benzene with olefins using as catalysts clays which can be repeatedly regenerated by a benzene wash and which can survive a carbon burn without losing its activity and stability as an alkylation catalyst. A broad embodiment is the use of a delaminated or pillared tetrahedrally charged clay as the catalyst. Another embodiment is the process of alkylating benzene with olefins using pillared saponites and beidellites for a time sufficient to afford the deactivated pillared clay, regenerating the activity of the deactivated pillared clay by washing the deactivated pillared saponite or beidellite with benzene, and reusing the regenerated pillared clay in benzene alkylation with olefins. In a more specific embodiment the clay is an ACH-pillared tetrahedrally charged clay such as saponite. In a yet more specific embodiment benzene is alkylated by detergent range olefins using ACH-pillared saponite regenerated by washing with benzene at a temperature between 100° and 250° C.

DESCRIPTION OF THE INVENTION

Whereas clays as a class are known catalysts for the alkylation of benzene by olefins, they are not commercially used because of their lower activity relative to silica-aluminas and, perhaps more importantly, because they are not regenerated by a benzene wash. Additionally, days as a class do not readily survive a carbon burn. However, we have found that tetrahedrally charged clays, and especially pillared saponites and beidellites, are exceptional in these respects, with characteristics more typical of silica-aluminas than of other clays. The tetrahedrally charged clays appear to be more acidic than other days, which probably is responsible for these materials exhibiting higher than expected activity. The tetrahedrally charged clays of this invention show a linearity in detergent alkylation comparable to the silica-aluminas at the same alkylation conditions, but most importantly are readily regenerated by a simple benzene wash, which is different from the other days we have tested. Finally, the tetrahedrally charged clays of this invention are stable to a carbon burn.

The feedstocks containing the alkylating agent which are used in the practice of that branch of our invention applicable to detergent alkylation normally result from the dehydrogenation of paraffins. Since the entire dehydrogenation reaction mixture often is used, the reaction is not run to completion to minimize cracking, isomerization, and other undesirable and deleterious byproducts. The branched olefins which are formed are not removed, yet the total amount of nonlinear alkylbenzene formed still must be sufficiently small that the monoalkylate meets the requirements of 90% linearity. The polyolefins formed during dehydrogenation are minimized in the feedstocks used in the practice of this invention. Consequently the feedstocks are largely a mixture of unreacted paraffins and unbranched, linear monoolefins which typically are in the C6–C20 range, although those in the C8–C16 range are preferred in the practice of this invention, and those in the C10–C14 range are even more preferred. Unsaturation may appear anywhere on the linear monoolefin chain; there is no requirement as to the position of the double bond, but only a requirement as to the linearity of the olefin. See R. A. Myers, "Petroleum Refining Processes", 4-36 to 4-38. (McGraw-Hill Book Company), 1986.

In the broader case the alkylating agent is an olefin, an alcohol, or an alkyl halide containing from 1 up to about 24 carbon atoms. Where the alkylating agent is an olefin the latter may be either branched or unbranched and also may be substituted with, for example, an aromatic substituent. Examples of suitable olefins include ethylene, propylene, the butenes, pentenes, hexenes, heptenes, octenes, nonenes, decenes, undecenes, dodecenes, tridecenes, tetradecenes, pentadecenes, hexadecenes, heptadecenes, octadecenes, nonadecenes, eicosenes, heneicosenes, docosenes, tricosenes, and tetracosenes. Further examples include styrene, phenylpropene, phenylbutene, phenylpentene, phenylhexene, and so forth.

Another class of alkylating agents which may be used in the practice of our invention are alcohols. Like the olefins, the alkyl chain in the alcohol may be branched or unbranched and the hydroxyl group may be found anywhere on the alkyl chain. That is, there is no particular requirement as to the spatial position of the hydroxyl moiety on the alkene chain. Examples of alcohols which may be successfully used in our invention include methanol, ethanol, propanol, butanol, pentanol, hexanol, heptanol, octanol, nonanol, decanol, undecanol, tetradecanol, and so forth. Especially relevant to this branch of the invention is methanol as the alcohol.

The last of the three classes of alkylating agents which may be frequently used in the practice of this invention are alkyl halides. Alkyl chlorides are probably the most widely used alkyl halides, but alkyl bromides also may be successfully used in the practice of our invention. As with alcohols, the paraffinic chain may be either branched or unbranched and the halogen may be found at any position along the chain. Suitable examples of alkyl halides include propyl chloride, propyl bromide, butyl chloride, butyl bromide, pentyl chloride, pentyl bromide, hexyl chloride, hexyl bromide, heptyl chloride, heptyl bromide, benzyl chloride, benzyl bromide, xylyl chloride, xylyl bromide, phenethyl chloride, phenethyl bromide, allyl chloride, allyl bromide, butenyl chloride, butenyl bromide, and so forth.

Where the process is detergent alkylation, the linear monoolefins in the feedstock are reacted with benzene. Although the stoichiometry of the alkylation reaction requires only 1 molar proportion of benzene per mole of total linear monoolefins, the use of a 1:1 mole proportion results in excessive olefin polymerization and polyalkylation. That is, the reaction product under such conditions would consist of not only the desired monoalkylbenzenes, but would also contain large amounts of the dialkylbenzenes, trialkylbenzenes, possibly higher polyalkylated benzenes, olefin dimers, trimers, etc., and unreacted benzene. On the other hand, it is desired to have the benzene:olefin molar ratio as close to 1:1 as possible to maximize benzene utilization and to minimize the recycle of unreacted benzene. The actual molar proportion of benzene to total monoolefins will therefore have an important effect on both conversion and, perhaps more importantly, selectivity of the alkylation reaction. In order to carry out alkylation with the conversion, selectivity, and linearity required using the catalysts of our process, a total benzene:linear monoolefin molar ratio of from 5:1 up to as high as 30:1 is recommended, although the process normally operates satisfactorily at a total benzene:linear monoolefins molar ratio between about 8:1 and about 20:1.

In the more general case the alkylating agent is reacted with an alkylatable aromatic compound. Such aromatic compounds are selected from the group consisting of benzene, naphthalene, anthracene, phenanthracene, and substituted derivatives thereof. The most important class of substituents are alkyl moieties containing from 1 up to about 20 carbon atoms. Another important substituent is the hydroxyl moiety as well as the alkoxy moiety whose alkyl group also contains from 1 up to 20 carbon atoms. Where the substituent is an alkyl or alkoxy group, a phenyl moiety also can be substituted on the paraffinic chain. Although unsubstituted and monosubstituted benzenes, naphthalenes, anthracenes, and phenanthrenes are most often used in the practice of this invention, polysubstituted aromatics also may be employed. Examples of suitable alkylatable aromatic compounds include benzene, naphthalene, anthracene, phenanthrene, biphenyl, toluene, xylene, ethylbenzene, phenol, anisole, propylbenzene, butylbenzene, pentylbenzene, hexylbenzene, heptylbenzene, octylbenzene, and so forth; ethoxy-, propoxy-, butoxy-, pentoxy-, hexoxybenzene, and so forth.

Where the process is detergent alkylation, the benzene and linear monoolefins in the $C_6$–$C_2$ range, are reacted in the presence of a catalyst under alkylation conditions. These alkylation conditions include a temperature in the range between about 80° C. and 150° C., and preferably in the range from 90° to 135° C. Since the alkylation is conducted as a liquid phase process, pressures must be sufficient to maintain the reactants in the liquid state. The requisite pressure necessarily depends upon the feedstock and temperature, but normally is in the range of 200–1000 psig (1379–6985 kPa), and most usually 300–500 psig (2069–3448 kPa).

In the more general case, there is a wide variation in the alkylation conditions of an alkylatable aromatic compound by an alkylating agent depending upon the reactivity of the two reactants. For example, for hydroxy benzenes (phenols) the hydroxyl moiety is found to be a quite activating group toward alkylation, and therefore the hydroxy benzenes are readily alkylated so that temperatures of no more than about 150° C. suffice. On the other hand, where the aromatic is an unsubstituted aromatic, such as benzene, and the alkylating agent is a lower olefin, such as propylene, temperatures as high as 400° C. may be necessary. Consequently, the temperature range appropriate for alkylation will be between about 60° and about 400° C., with the most usual temperature range being between 100° and 225° C. As regards pressures, since the alkylation is desirably conducted as a liquid phase process the reaction pressure must be sufficient to maintain the reactants in the liquid stage. This is the sole pressure requirement for the practice of this invention, and since a wide variety of alkylatable aromatics compounds and alkylating agents may be used in the practice of this invention it can be readily appreciated that there exists a wide variation in reaction pressure, from atmospheric up to as high as about 2000 pounds per square inch (14,000 kPa).

The class of catalysts which may be used in the practice of our invention are the tetrahedrally charged clays, both delaminated and pillared, with the catalysts of choice being pillared, interlayered tetrahedrally charged clays as exemplified by pillared saponites and beidellites. The naturally occurring tetrahedrally charged clays are composed of semi-crystalline alumino-silicate layers (lamellae) held together by van der Waals and electrostatic forces. Anionic charges on the siliceous layers are neutralized by cations in the interlamellar spaces. When these cations are large oligomers of inorganic cations such as $Fe^+$ or $Cr^{+3}$, or when they are metal hydroxy polymer cations such as $[Al_{13}O_4(OH)_{24}(H_2O)_{12}]^{+7}$ or $[Zr(OH)_2 \cdot 4H_2O]_4^{8+}$, introduced during the preparation of the layered clays, the cations act as pillars, propping the tetrahedrally charged clay layers apart to afford a pillared interlayered clay.

Pillared clays are characterized by having an interlamellar distance after drying at 150°C. of more than 5 Angstroms and by having substantial microporosity, i.e., a micropore volume in the range of about 0.15–0.4 cc per gram where the micropore diameter was no more than about 20 Angstroms. Although small, non-oligomeric metal cations may occur in the interlamellar region of layered clays such materials are not pillared clays; upon heating such materials (to effect dehydration) the interlamellar space collapses because a small, unhydrated metal cation is unable to act as a pillar to hold apart adjacent layers. Such a collapse upon heating distinguishes metal-exchanged but non-pillared saponites and heidellites from pillared saponites and beidellites.

Among the metal cations whose oligomers may be used are known iron (III), chromium (III), aluminum, titanium (IV), and zirconium (IV). Pillared saponites and heidellites, whose pillars are aluminum chlorohydrate—a polymeric metal complex with the empirical formula $Al_{2-n}(OH)_{2n}Cl_6$, where n has a value of about 4 to 12—are preferred and are referred to as ACH clays.

A rare earth aluminum chlorohydrate (ACH) clay is an ACH-pillared clay as described above which is modified to include one or more rare earth elements, i.e., elements of atomic number 57 through 71, such as cerium, lanthanum, neodymium, europium, samarium, praesodymium, etc. The ACH polymer used in the preparation of the pillared clay is modified with the rare earth by adding a soluble rare earth salt, preferably a water soluble rare earth salt. Examples of rare earth salts are the nitrates, halides, sulfates and acetates. Preferred rare earth elements are cerium and lanthanum with cerium nitrate and lanthanum nitrate being the preferred salts. The rare earth is introduced into the polymer or oligomer structure by mixing the rare earth salt either in solution (water preferred) or as a solid with the ACH. The mixture is refluxed at a temperature of about 105° to about 145° C. for a time of about 24 to about 100 hours. The molar ratio of rare earth (expressed as oxide, e.g., $CeO_2$) to alumina ($Al_2O_3$) in the solution prior to refluxing is from about 1:52 to about 1:1.

When pillars of aluminum chlorohydrate containing one or more rare earths are introduced into the tetrahedrally charged clays, the resulting pillared clays are referred to as rare earth ACH pillared tetrahedrally charged clays, e.g., Ce-ACH pillared saponite, La-ACH pillared beidellite, and so on. The ACH or rare earth ACH clays are prepared by means well known in the art such as adding the desired clay to an ACH or rare earth ACH solution, stirring, filtering, redispersing with water (one or more times), isolating, drying and calcining at about 500° to about 800° for a time sufficient to fix the structure (preferably about 3 hours). Any and all mixtures of the clays enumerated above can be used in the invention.

More generally, the pillared clays of this invention are calcined at a temperature in the range of 350° to about 650° C. For catalysts of high activity it is found that calcination in the range of 350° to about 425° C. is preferred. The resulting pillared clays are more active than other clays without any detrimental effects on linearity. Calcination conditions do have a significant effect on, e.g., linearity, but simple experimentation will determine the optimum calcination conditions for a particular clay catalyst of this invention.

As with all catalysts, the tetrahedrally charged clays of this invention become deactivated with time in use. Quite commonly detergent alkylation is run under conditions where initially there is 100% conversion of olefins. Equally commonly, a catalyst is often removed from service (the reaction cycle) and said to be "deactivated" when olefin conversion drops to the 97–98% level, at which point catalyst activity is restored during a regeneration cycle. In some processes catalyst may be removed from the reaction cycle and put into its regeneration cycle at predetermined time intervals, irrespective of any observable decrease in olefin conversion. The point where the catalyst is judged to be sufficiently deactivated to be removed from its reaction cycle and placed in its regeneration cycle is quite dependent on the particulars of the process chosen, and even on the practices of a particular operator. For the purpose of this application we will assume that a deactivated catalyst may be continued to be used in the reaction cycle until olefin conversion drops to no less than about 80%, recognizing that in most cases a deactivated catalyst will be removed from its reaction cycle much before conversion drops so low. For purposes of this application a "deactivated catalyst" is one which has less activity than the catalyst had at the beginning of its current reaction cycle.

The deactivated catalysts of our invention are, quite unexpectedly, regenerated by a simple benzene wash. Wash temperatures must be at least as great as alkylation temperature, and usually are substantially greater. For example, it has been found that a benzene wash at about 250° C. for 6 hours at an LHSV of 3 $hr^{-1}$, followed by 18 hours at an LHSV of 1.5 $hr^{-1}$, restores essentially all of the catalyst activity, even when the catalyst has been so deactivated as to effect only about 80% conversion. Of course, when the catalysts of our invention experience lesser deactivation they will be regenerated under less severe conditions (e.g., lower wash temperature, shorter wash time). More generally, our catalysts may be regenerated by washing with from about 10 to about 75 volumes of benzene at a temperature between about 100° C. and about 250° C. Our catalysts are capable of many regenerations without substantial reduction in the catalytic activity or without a substantial reduction in catalyst life. However, when the reaction cycle is reduced to an unacceptable level, which is usually on the order of 30% of the original reaction cycle, it is subjected to a carbon burn to remove accumulated organics not removed by benzene and to remove accumulated coke. A carbon burn in air at temperatures between 450°–550° C. is found to be sufficient to restore not only catalytic activity but also catalyst lifetime (as measured by its reaction cycle time) to its initial values.

Alkylation of benzene by the detergent-range linear monoolefins of this invention may be conducted either as a batch method or in a continuous manner, although the latter is greatly preferred and therefore will be described in some detail. The composites of this invention used as catalyst may be used as a packed bed or a fluidized bed. Feedstock to the reaction zone may be passed either upflow or downflow, or even horizontally as in a radial bed reactor. The admixture of benzene and the feedstock containing the total linear monoolefins is introduced at a total benzene:olefin ratio of between 5:1 and 30:1, although usually the ratio is in the range between about 8:1 and 20: 1. In one desirable variant olefin may be fed into several discrete points within the reaction zone, and at each zone the benzene:olefin ratio may be greater than 30:1. However, the total benzene:olefin ratio used in the foregoing variant of my invention still will be within the stated range. The total feed mixture, that is, benzene plus feedstock containing linear monoolefins, is passed through the packed bed at a liquid hourly space velocity (LHSV) between about 0.3 and about 6 $hr^{-1}$ depending upon alkylation temperature, how long the catalyst has been used, the ratio of silica to alumina and fluoride level in the catalyst, and so on. The temperature in the reaction zone will be maintained at between about 80° and about 150° C., and pressures generally will vary between about 200 and about 1000 psig (1379–6895 kPa) to ensure a liquid phase alkylation. After passage of the benzene and linear monoolefin feedstock through the reaction zone, the effluent is collected and separated into benzene, which is recycled to the feed end of the reaction zone, paraffin, which is recycled to the dehydrogenation unit, and alkylated benzenes. The alkylated benzenes are usually further separated into the monoalkyl benzenes, used in subsequent sulfonation to prepare the linear alkylbenzene sulfonates, and the oligomers plus polyalkylbenzenes. Since the reaction usually goes to at least about 98% conversion, little unreacted monoolefin is recycled with paraffin.

For alkylation other than detergent alkylation, i.e., in the more general case, the reaction between the alkylatable aromatic compound and the alkylating agent will also be performed generally as described above. Whether the aromatic or the alkylating agent is used in excess depends upon the relative economics of the process, the desirability of the predominance of a particular product, the tendency toward oligomerization of, for example, the olefin, and so forth. However, in general the ratio of the alkylatable aromatic substrate and alkylating agent may range between about 1:20 and 20:1. As stated previously, alkylation temperatures will be in the range of 60°–400° C., although temperatures between 100° and 225° C. are more the norm. Pressures will be adequate to ensure a liquid phase alkylation and usually will be no more than about 500 pounds per square inch, although in the case of lower olefins higher temperatures up to perhaps 2,000 psig may be employed. Whether there is recycling of any of the unreacted components will depend, inter alia, upon the extent of conversion, the economic value of the reactant, the ease with which the unreacted materials are separated from the reaction products, and so forth.

The following examples are solely for purposes of illustration. They show in detail how the invention claimed below may be effected but our examples are not intended to limit the invention in any way.

EXAMPLES

Preparation of Materials

The following descriptions are representative of the methods used.

Preparation of Ce-ACH Sol $Ce(NO_3)_3 \bullet 6H_2O$ (4.8 g) were dissolved in 66 g of ACH sol (50 weight percent solution, obtained from Rebels) in a Parr Teflon Liner (125 cc). The liner was placed in a Parr Reactor and the reactor was placed in a 135° C. oven. After 5 days, the reactor was removed from the oven.

Preparation of Ce-ACH Pillared Clay

In a 3000 ml, three neck round bottom flask equipped with a condenser, an overhead stirrer and a thermometer was placed 2100 g of deionized (DI) $H_2O$ and 137 g of Ce-ACH sol. The temperature was brought up to 95° C. After 30 minutes, 54 g of saponite clay (SapCa, obtained from the Clay Minerals Society) was added while stirring. The slurry was maintained at 95° C., with stirring for 1 hour. The slurry was recovered using a centrifuge. The clay was washed until Cl free and dried at 60° C. for 16 hours. The clay was then calcined at 600° C. for 2 hours. The clay was characterized using XRD ($d_{001}$=26.5 Å) and $N_2$ adsorption (BET SA=550 $m^2/g$).

Preparation of ACH Pillared Saponite Clay

In a 3000 ml, three neck round bottom flask equipped with a condenser, an overhead stirrer and a thermometer was placed 2100 g of DI $H_2O$ and 60 g of ACH sol. The temperature was brought up to 95° C. After 30 minutes, 54 g of saponite clay (SapCa, obtained from the Clay Minerals Society) was added while stirring. The slurry was maintained at 95° C., with stirring for 1 hour. The slurry was recovered using a centrifuge. The clay was washed until Cl free and dried at 60° C. for 16 hours. The clay was then calcined at 600° C. for 2 hours. The clay was characterized using XRD ($d_{001}$=17.8 Å) and $N_2$ adsorption (BET SA=267 $m^2/g$).

Preparation of ACH Pillared Beideilite Clay

In a 3000 ml, three neck round bottom flask equipped with a condenser, an overhead stirrer and a thermometer was placed 2100 g of DI $H_2O$ and 60 g of ACH sol. The temperature was brought up to 95° C. After 30 minutes, 50 g of beidellite clay (prepared synthetically following U.S. Pat. No. 5,296,427) was added while stirring. The slurry was maintained at 95° C., with stirring for 1 hour. The slurry was recovered using a centrifuge. The clay was washed until Cl free and dried at 60° C. for 16 hours. The clay was then calcined at 600° C. for 2 hours. The clay was characterized using XRD ($d_{001}$=17.3 Å) and $N_2$adsorption (BET SA=180 $m^2/g$).

Preparation of Synthetic Delaminated Saponite Clay

In a 2000 ml, three neck round bottom flask equipped with a condenser, an overhead stirrer and a thermometer was placed 378 g of $MgSO_4 \bullet 7H_2O$ in 510 g of DI water. The temperature was brought up to 85° C. To this was added a solution of 377.6 g waterglass (29.95% $SiO_2$), 10.3 g NaOH in 259 g DI water with heavy mixing. The resulting slurry was then heated with stirring for 60 minutes. To this slurry was added a solution of 62 g $Na_2CO_3 \circ H_2O$, 82 g NaOH, 29.6 g $NaAlO_2$ in 500 g of DI water. After stirring the resulting slurry for an additional 60 minutes, the slurry was crystallized in a Parr reactor at 200° C. for 8 hours. The product was recovered by filtration and the solid washed with 2 L of water. The product was dried at 110° C. XRD results on the product show it to be a poorly crystallized smectite clay. The BET surface area of the clay was 320 $m^2/g$.

Preparation of Ammonium Exchanged Delaminated Saponite Clay

In a 2000 ml beaker 55 g $NH_4Cl$ were dissolved in 1000 ml of water. To this solution was added 25 g of the delaminated saponite clay. The solution was stirred for 30 minutes and then left quiescently for 24 hours. The clay was recovered by filtration. The procedure was repeated. The clay was then washed with 2 L of DI water and then dried at 110° C. The sample was then calcined at 400° C. for 2 hours. The BET surface area of the clay was 260 m²/g.

General Alkylation Procedure

A reactor was packed with 75 cc (48.1 g) of the foregoing catalyst. A typical feedstock contained 57.5% w/w benzene and 42.5% w/w of the reaction mixture resulting from dehydrogenation of normal paraffins mainly in the $C_9$–$C_{14}$ range. Analytical data for a representative paraffin dehydrogenation product used in these examples is given in Table 1.

TABLE 1

| COMPOSITION | WEIGHT PERCENT |
|---|---|
| Non-normal | 7.8 |
| n-paraffin | 80.9 |

TABLE 1-continued

| COMPOSITION | WEIGHT PERCENT |
|---|---|
| n-olefin | 11.3 |
| $C_9$ Paraffin | 0.1 |
| $C_9$ Olefin | <0.1 |
| $C_{10}$ Paraffin | 8.1 |
| $C_{10}$ Olefin | 1.0 |
| $C_{11}$ Paraffin | 31.6 |
| $C_{11}$ Olefin | 4.0 |
| $C_{12}$ Paraffin | 24.9 |
| $C_{12}$ Olefin | 3.6 |
| $C_{13}$ Paraffin | 15.9 |
| $C_{13}$ Olefin | 2.6 |
| $C_{14}$ Paraffin | 0.3 |
| $C_{14}$ Olefin | 0.1 |

The feed, which had a benzene:olefin ratio of 25, was supplied at a liquid hourly space velocity of 2.0 and reaction was conducted at 100° C. and at 500 psig total pressure. Table 2 below summarizes some data for ACH saponite and compares it with Ce ACH montmorillonite and a 75-25 silica-alumina, and also contains data for an ACH saponite subjected to a carbon burn as follows. The sample (after 1 reaction cycle) was heated from room temperature in a nitrogen flow (5 liters per minute) to 450° C. at 1.5° C. per minute. A carbon burn was conducted at 400° C. with 0.5, 1, 2, 10, and 20% oxygen. When the carbon monoxide and carbon dioxide levels each were 0.05%, the next highest oxygen level was used. After completion of the foregoing carbon burn, the sample was ramped at 10° C. per minute to 550° C. under 100% nitrogen. At 550° C. a carbon burn was conducted with 2, 5, 10, and 20% oxygen, using the same method as described above to determine when to go to the next level of oxygen.

TABLE 2

Detergent Alkylation with Clays; Conversion of C12 Olefin

| Catalyst | 3:1 Silica Alumina | ACH Saponite | ACH Bentonite | Ce ACH PILC | ACH Saponite[a] |
|---|---|---|---|---|---|
| Linearity | 90.4 | 91.8 | 94.4 | 94.4 | 92.4 |
| Hours on Stream | | | C12 CONVERSION | | |
| 1 | | | | | |
| 2 | | | | | |
| 3 | | | | | |
| 4 | 93.0 | 99.4 | 85.1 | 94.1 | |
| 5 | 82.7 | 96.2 | 56.3 | 81.4 | 95.2 |
| 6 | 82.9 | 95.8 | 50.1 | 76.7 | 93.7 |
| 7 | | 95.2 | 45.8 | 71.5 | 91.8 |
| 8 | 79.7 | 94.1 | 42.8 | 67.9 | 89.7 |
| 9 | 78.2 | 91.9 | 40.5 | 65.0 | 88.2 |
| 10 | 75.8 | 91.1 | 38.5 | 62.0 | 86.7 |
| 11 | 74.6 | 90.4 | 37.4 | 61.8 | 85.5 |
| 12 | 73.7 | 89.9 | 36.4 | 60.4 | 84.0 |
| 13 | 71.0 | 89.1 | 36.7 | 58.2 | 82.6 |
| 14 | 71.1 | 88.8 | 35.5 | 55.7 | 81.8 |
| 15 | 71.7 | | 35.0 | 53.8 | 81.1 |
| 16 | 71.3 | 87.1 | 33.2 | 52.6 | 80.6 |
| 17 | 70.9 | 86.7 | 33.2 | 51.3 | 79.8 |
| 18 | 70.0 | 86.3 | 32.2 | 50.4 | 79.9 |
| 19 | 69.1 | 85.8 | 30.9 | 48.9 | 78.8 |
| 20 | 68.8 | 85.9 | 37.8 | 48.2 | 78.3 |
| 21 | 68.0 | 84.5 | 36.2 | 47.3 | 78.1 |
| 22 | 67.4 | 83.8 | 33.8 | 46.4 | 76.6 |
| 23 | 66.8 | 83.3 | 32.9 | 44.7 | 76.8 |
| 24 | 66.7 | | 31.0 | 44.7 | |

[a]Subjected to carbon burn after 1 reaction cycle; see text.

These results show that the tetrahedrally charged clay (ACH Saponite) deactivates much slower than the other clays and is reactivated after a carbon burn. It is believed this is the first demonstration of reactivation of a clay catalyst in detergent alkylation by a carbon burn.

At the end of a 24 hour reaction cycle an ACH saponite catalyst was regenerated with a benzene wash at 250° C. over the next 24 hours at a space velocity of 3 hr$^{-1}$ for 6 hours followed by 1.5 hr$^{-1}$ for 18 hours. Results of the regenerated (benzene wash) catalyst are given in Table 3.

TABLE 3

Regeneration of ACH Saponite; Conversion of C12 Olefin

| | Cycle 1 | Cycle 2 | Cycle 3 |
|---|---|---|---|
| LINEARITY | 90.7 | 90.7 | 90.4 |
| Hours on Stream | | C12 CONVERSION | |
| 1 | | | |
| 2 | | | |
| 3 | | 97.1 | 98.9 |
| 4 | 98.2 | 97.3 | 97.0 |
| 5 | 94.9 | 96.0 | 96.8 |
| 6 | 93.0 | 95.2 | 96.1 |
| 7 | 91.4 | 92.0 | 92.9 |
| 8 | 89.7 | 90.4 | 91.6 |
| 9 | 88.3 | 88.5 | 90.1 |
| 10 | 87.6 | 87.1 | 92.6 |
| 11 | 86.8 | 86.3 | 88.3 |
| 12 | 86.4 | 85.4 | 86.2 |
| 13 | 85.5 | 84.6 | 85.8 |
| 14 | 85.1 | 83.6 | 85.1 |
| 15 | 84.7 | 82.8 | 84.3 |
| 16 | 84.4 | 82.7 | 83.4 |
| 17 | | 81.6 | 82.5 |
| 18 | | 81.1 | 82.3 |
| 19 | 83.8 | 80.3 | 81.8 |
| 20 | 82.3 | 79.9 | 80.9 |
| 21 | 81.9 | 79.4 | 80.5 |
| 22 | 81.6 | 79.3 | 80.2 |
| 23 | 81.3 | 78.7 | 79.8 |
| 24 | 80.9 | 78.5 | 79.0 |

Note that the ACH saponite of this table was calcined at different conditions than that used for the sample of Table 2, and that different calcination temperatures could be expected to afford somewhat different results, especially as to linearity.

What is claimed is:

1. A process for the alkylation of benzene comprising:

a) reacting under alkylating conditions benzene with one or more linear monoolefins in a feedstock containing at least one linear monoolefin, said alkylating conditions including reacting from about 5 to about 30 molar proportions of total benzene for each molar proportion of total linear monoolefins at a temperature from about 80° C. to about 150° C. and a pressure from about 200 to about 1000 psig, in the presence of a tetrahedrally charged clay as catalyst to obtain alkylated benzenes with an initial conversion of at least 98% of said monoolefins;

b) continuing reacting benzene and said monoolefins under alkylating conditions until, as a consequence of catalyst deactivation, conversion of said monoolefins decreases to no less than about 80% conversion;

c) reactivating the deactivated catalyst by heating the catalyst with from about 10 to about 75 volumes of benzene at a temperature from about 100° to about 250° C. for a time sufficient to afford a reactivated catalyst whose activity is sufficient to effect at least 98% conversion of said monoolefins in their reaction with benzene; and d) repeating stage a).

2. The method of claim 1 where the molar ratio of benzene to linear monoolefins is from about 8 to about 20.

3. The process of claim 1 where the temperature is between about 90° C. and about 135° C.

4. The process of claim 1 where the monoolefins have from about 6 to about 20 carbon atoms.

5. The process of claim 4 where the monoolefins have from about 8 to about 16 carbon atoms.

6. The process of claim 5 where the monoolefins have from about 10 to about 14 carbon atoms.

7. The process of claim 1 where the tetrahedrally charged clay is delaminated.

8. The process of claim 1 where the tetrahedrally charged clay is pillared.

9. The process of claim 1 where the tetrahedrally charged clay is a saponite or beidellite.

10. The process of claim 9 where the tetrahedrally charged clay is a pillared saponite or pillared beidellite.

11. The process of claim 10 where the pillars of the pillared saponite or beidellite are oligomers of metal cations, where the metal is selected from the group consisting of iron (III), chromium (III), aluminum, titanium (IV), and zirconium (IV).

12. The process of claim 10 where the pillars of the pillared saponite or beidellite are metal hydroxy polymer cations and said metal is aluminum, titanium, or zirconium.

13. The process of claim 10 where the pillars of the pillared saponite or beidellite are aluminum chlorohydrate.

14. The process of claim 10 where the catalyst is a rare earth aluminum chlorohydrate pillared saponite or beidellite.

* * * * *